United States Patent [19]

Fourman et al.

[11] Patent Number: 4,963,591

[45] Date of Patent: Oct. 16, 1990

[54] COSMETIC COMPOSITIONS

[75] Inventors: Robert G. Fourman, Plainsboro; Richard P. Dixon, Aberdeen; Hans Breuer, Bridgewater, all of N.J.

[73] Assignee: Carter-Wallace Inc., New York, N.Y. ; a part interest

[21] Appl. No.: 809,102

[22] Filed: Dec. 16, 1985

[51] Int. Cl.$^5$ .................. A61K 7/021; A61K 7/06; A61K 7/13; A61K 7/32; A61K 7/40; A61K 7/48

[52] U.S. Cl. .................. 514/944; 8/405; 8/406; 106/189; 424/59; 424/60; 424/63; 424/65; 424/68; 424/70; 424/73; 424/195.1; 514/37; 514/152; 514/770; 514/773; 514/817; 514/827; 514/828; 514/830; 514/844; 514/845; 514/846; 514/847; 514/848; 514/852; 514/857; 514/858; 514/859; 514/860; 514/867; 514/862; 514/863; 514/864; 514/865; 514/873; 514/880; 514/881; 514/882; 514/886; 514/887; 514/918; 514/919

[58] Field of Search ............ 424/DIG. 10, 195.1; 106/189; 514/944

[56] References Cited

U.S. PATENT DOCUMENTS 2,435,005 1/1948 Huppke et al. ............... 424/60
3,186,912 6/1965 Beamer ................ 424/DIG. 10

FOREIGN PATENT DOCUMENTS 0106193 4/1984 European Pat. Off. ............ 424/365
1173447 7/1964 Fed. Rep. of Germany ...... 106/189
2455459 1/1981 France .................. 424/DIG. 10
309711 5/1972 U.S.S.R. ................ 424/DIG. 10
796308 6/1958 United Kingdom ............. 106/189

*Primary Examiner*—Dale R. Ore
*Attorney, Agent, or Firm*—Kevin B. Clarke

[57] ABSTRACT

Skin care cosmetic formulations which include a cellulosic polymer/solvent system capable of dispersing thin, substantive films on the skin are disclosed.

2 Claims, No Drawings

COSMETIC COMPOSITIONS

The present invention relates to cosmetic formulations which include a non-aqueous polymer/solvent film-forming system capable of dispersing thin, substantive films on the skin which films are characterized by good tactile properties as well as by the ability to provide uniform dispersion of the active material on the skin as well as the ability to keep the active material on the skin for prolonged periods of time.

More particularly, the present invention relates to film-forming cosmetic compositions comprising a cellulosic polymer/solvent system and cosmetically active materials which when applied to the skin, provide thin, substantive, flexible films which do not crack, peel or flake; which are water-proof or highly resistant to water; which do not have an oily, greasy, sticky or waxy feel and which provide good, long-term adhesion of cosmetically active materials to the skin; and which, in appropriate circumstances, provide for slow release of the active material over prolonged periods of time.

Moreover, this invention relates to polymer/solvent film-forming cosmetic compositions which when applied to the skin provide thin, flexible, substantive films which have good tactile properties and which prevent loss of water from the skin surface to the environment.

Since increased moisture content is believed to be responsible for increasing the flexibility of the skin, the application of oils, water in oil or oil in water emulsions to the skin so as to form a barrier which reduces the escape of moisture from the skin is widely practiced cosmetic art.

The hydrocarbons such as petrolatum, mineral oil, paraffin wax and ozokerite, such as disclosed in U.S. Pat. No. 4,389,418, as well as many other emollient materials, have long been used in skin creams and lotions. These materials function as emollients by covering the skin with a hydrophobic occlusive film which prevents water loss from the skin surface to the environment. In addition, animal fats and oils such as lanolin and its various derivatives such as acetylated lanolins, have been used in many skin creams and lotions as the emollient of choice, depositing on the skin, films that are hydrophobic, waxy, protective and emollient in character.

While the foregoing emollient materials have valuable moisturizing and skin softening properties when utilized in skin creams and lotions, they also possess undesirable effects in that they lack good tactile properties and generally impart to the skin an uncomfortable feeling of warmth in addition to a sticky, oily, greasy or waxy feel.

There is therefore a continuing need for the development of new and improved skin conditioning compositions which impart beneficial effects to the skin.

It is an object of this invention to provide non-aqueous skin treating and conditioning compositions which when applied to the skin, leave a substantive, thin film on the skin surface which is characterized by good tactile properties and resistance to water.

The foregoing and other objects will become apparent from the description of the invention to follow.

In accordance with the present invention, it has now been found that the addition of a water insoluble cellulosic polymer/solvent system to non-aqueous skin care formulations which comprise well-known cosmetic actives, permits the dispersion of a fine, thin, substantive film over the skin surface which is flexible, non-flaking and free of any sticky, oily, greasy or waxy feel. The films provide for uniform dispersion of the active, good long term adherence of the active to the skin and high resistance to removal by water or abrasion.

The compositions of the present invention may be applied to the skin, i.e., the arms, the legs, the entire body, where conditioning or treatment is desired, by smoothing it over the skin.

The cellulosic polymer/solvent systems of the present invention find utility in sunscreen, acne, antifungal, poison ivy, poison oak, poison sumac, diaper rash, insect bite, analgesic, anesthetic, antipruritic, moisturizers, astringents, antibiotic, hemorrhoid, make-up, deodorant, antiperspirant, hair dye and other lotions and creams designed for topical application.

The compositions of the present invention comprise a water-insoluble cellulosic ether, such as ETHOCEL STANDARD, a tradenamed material marketed by Dow Chemical Company, having an ethoxyl content above about 47% preferably an ethoxyl content of from 48.0 to 49.5% in amounts ranging from 0.1% to 10.0%, preferably about 0.75 to about 1.60% by weight of the total composition and a solvent for the cellulosic polymer which is a lower aliphatic alcohol such as ethanol, propanol or isopropanol which is present in amounts ranging from about 20% up to about 95% or above by weight of the total composition. The remaining essential ingredients of the compositions are cosmetic ingredients chosen to provide a specifically tailored cosmetic composition having particular beneficial effects, i.e., sunscreens, antifungals, antibiotics, insect repellents, moisturizers, astringents, deodorants, and the like. The active materials are present in widely varying amounts depending upon the particular actives selected and the results desired.

Other conventional additives commonly employed in cosmetic compositions may also be employed such as fragrances, preservatives, emollients, emulsifiers, thickeners, surfactants and the like so long as they are compatible with the polymer/solvent system.

Copending U.S. application Ser. No. 580,748 filed February 16, 1984, now U.S. Pat. No. 4,518,593, discloses compositions comprising a film-forming cellulosic polymer; a solvent; an ultraviolet sunscreening agent; an emollients and optionally, a plasticizing agent. In addition, the compositions may include small but effective amounts of opacifiers, surfactants, fragrances and other compatible agents to obtain desired cosmetic esthetics.

In accordance with a specific embodiment of this invention, a sunscreen/insect repellent comprises the film-forming cellulosic polymer, desirably a cellulosic ether which is present in the sunscreen compositions in amounts ranging from 0.1% to 10.0%, preferably 0.5% to 4.0% by weight of the total composition. The preferred cellulose ether is a cellulose ethyl ether having an ethoxyl content above about 48%.

The solvent is a solvent for the insect repellent as well as the cellulosic polymer and is preferably an aliphatic alcohol such as ethanol, propanol or isopropanol which is present in amounts ranging from about 10% to about 90% or above, preferably 20.0% to 50% by weight of the total composition.

The emollient materials are selected from among the hydrocarbon oils and waxes, as well as fatty acid esters such as butyl stearate, isopropyl stearate, isopropyl palmitate, isopropyl myristate and volatile silicone fluids composed of low molecular weight dimethyl siloxanes that have been assigned CTFA name cyclomethicone and are exemplified by Volatile Silicone 7207, a trademarked product of Union Carbide Corporation and the following trademarked product of Dow Corning Corporation: Dow Corning 244 Fluid and Dow Corning 245 Fluid. The emollient material is present in amounts ranging from 5.0% to 60.0%, preferably 20.0% to 45.0% by weight of the total composition.

The ultraviolet absorbing sunscreen and insect repellent are compatible with the emollients and desirably dissolved therein whereby clear, preferably water-white, compositions are obtained. The sunscreen material is selected from the group comprising the 2-ethyl-hexylester of 4-(dimethylamino) benzoic acid; dioxybenzone; ethylhexyl-p-methoxycinnamate; ethyl 4-[b15 (hydroxypropyl)]aminobenzoate; 3,3,5-trimethylyclohexy salicylate; 2-ethylhexyl2-cyano3, 3-diphenylacrylate; 2-ethylhexyl salicylate and mixtures thereof. The sunscreen material is present in amounts ranging from 1.0% to 20.0%, preferably 4.0% to 11.0% by weight of the total composition.

In the event, a volatile silicone fluid is employed as an emollient, a further desirable component in the compositions is a plasticizer for the cellulose film. The plasticizer is preferably selected from among the silicone resins listed under the CTFA name Dimethicones. The plasticizers are to be distinguished from the previously disclosed cyclomethicone volatile fluids in that the latter are low molecular weight, volatile dimethyl siloxanes whereas the former are higher organic content polymethyl siloxanes, polyphenylsiloxanes and combinations of polymethylsiloxanes with trimethyl siloxysilicate, exemplary materials are available from The General Electric Company under the Trademark GE Silocone 4267 and Dow Corning company under the trademarks Dow Corning 225 Fluid, Dow Corning 556 fluid and Dow Corning 1107 Fluid and Union Carbide under the trademark Union Carbide Silicone L-45.

If present in the composition, the plasticizer may be included in amounts ranging from about 0.1% to about 10.0%, preferably from about 0.1% to about 1.0% by weight of the total composition.

It has now been found that the foregoing compositions, which demonstrate water-proof sunscreening properties, also provide excellent insect repellency of unexpectedly long duration, when combined with insect repellents.

It has previously been proposed to provide cosmetic compositions which provide both sunscreening and insect repellent properties. Such properties are necessary and desirable when, during periods of warm weather, both workers and vationers, when outdoors, are subject to the dangers and the discomforts of an excess of ultraviolet rays and of biting insects.

U.S. Pat. No. 3,186,912 discloses water in oil emulsion systems based on imidazoline surfactants which are water repellent and contain both sunscreening and insect repellent agent. Likewise, U.S. Pat. No. 2,435,005 discloses insect repellent/sunscreening compositions which are gelatinous in nature and include acetone as a solvent and a film-forming system which is preferably a mixture of ethyl cellulose and shellac.

We have found that non-toxic, non-irritating compositions composed of a cellulosic polymer, as the sole film-forming component, a solvent, ultraviolet sunscreening agents, insect repellents and an emollient provide sunscreening/insect repellent compositions which demonstrate prolonged insect repellent properties, i.e. twelve hours or longer, as well as prolonged and high sun protection factors.

Moreover, when such compositions are applied to the skin, they leave an elegant clear, non-tacky, non-sticky film.

It was our expectation that the addition of an insect repellent to the aforesaid sunscreening compositions would result in diminished insect repellency due to the presence of the cellulosic film which would reduce the rate of evaporation of the repellent. To the contrary, it was unexpectedly found that the presence of the cellulosic film not only did not reduce or retard evaporation of the repellent, but rather provided repellent activity for prolonged periods without diminution of its effectiveness.

Optionally, the sunscreening/insect repellent compositions of the present invention may include plasticizing agents, opacifiers, surfactants, fragrances as well as other compatible materials which may be desired to enhance the cosmetic properties of the compositions.

The insect repellents useful in the present invention, which must not be capable of absorption through the skin, can be generally described as organic liquids essentially insoluble in water but freely soluble in alcohol, benzene and petroleum solvents. A particularly desirable compound is N, N-diethyl-m-toluamide but others that are likewise suitable are bicarboximide, N-octyl-bicycloheptene, and bi-N-propylisocinchomeronate.

The insect repellents are present in the compositions of the present invention in amounts ranging from about 5% to about 25% by weight of the total composition preferably about 12% to about 18% by weight.

The water-proof sunscreen compositions of the present invention may be formulated by simply and mixing all of the components. However, it is preferred to first dissolve the cellulosic material in the solvent prior to and mixing with the remaining components.

The example which follows sets forth the preferred embodiment of the present invention:

FORMULA 1

| PRODUCT | % W/W |
|---|---|
| Sunscreen/insect repellant | |
| Ethanol, 200 proof | 30.5 |
| Ethocel (Std.-100 Visc.) | 1.0 |
| Silicone 7207 (Union Carbide) | 30.0 |
| G.E. Silicone SS 4267 | 0.5 |
| Escalol 507 | 8.0 |
| Parsol MCX | 7.5 |
| Octyl salicylate | 5.0 |
| Dermol 105 (Isodecyl Neopentanoate) | 2.0 |
| MCK Diethytoluamide | 15.0 |
| Firmenich Perfume 47.297 | 0.5 |
| | 100.0% |

The foregoing composition when spread on the skin, is quickly absorbed into the skin, leaving an elegant, greaseless, non-tacky, dry, film, providing long lasting and effective insect repellency, superior sun protection factor, and superior resistance to removal of the active agents from the skin by perspiration or water as evidenced by standard whirlpool wash-off tests.

The following formulations serve to further illustrate the scope of utility of the cellulosic polymer/solvent system of the present invention and are not to be construed as limitative of the scope of the present invention.

| PRODUCT | FORMULA 2 | % W/W | ACTIVE MATERIALS |
|---|---|---|---|
| Dandruff, Psoriasis Seborrheic Dermatitis Preparations | Alcohol SDA 40 200° Salicyclic Acid Sulfur Ethocel Standard 100 Premium Volatile Silcone | 51.0 3.0 5.0 1.0 40.0 | Coal tar distillate 4% Coal tar extract 2 to 8.75% Coal tar solution 2.5 to 5% Coal tar, USP, .5 to 5% Pyrithione zinc 1 to 2% Pyrithione zinc .1 to .25% Salicyclic Acid 1.8 to 3% Selenium sulfide 1% Sulfur 2 to 5% Sulfur 2 to 5% with salicyclic acid 1.8 to 3% |

| PRODUCT | FORMULA 3 | % W/W | ACTIVE MATERIALS |
|---|---|---|---|
| Acne Lotion | Alcohol SDA 40 200° Ethocel Standard 100 Premium Benzoyl Peroxide | 89.0 1.0 10.0 | Benzoyl Peroxide 2.5 to 10% Resorcinol 2% when combined with 3 to 8% sulfur Resorcinol monoacetate 3% when combined with sulfur at 3 to 8% Salicyclic acid .5 to 2% Sulfur 3 to 10% |

| PRODUCT | FORMULA 4 | % W/W | ACTIVE MATERIALS |
|---|---|---|---|
| Antifungal Lotion | Alcohol SDA 40 200° Ethocel Standard 100 Premium Propylene Carbonate Tolnaftate | 57.49 1.51 40.00 1.0 | Iodochloryhydroxyquin 3% Miconazople nitrate 2% Nystatin 100,000 unit/gram Tolnaftate 1% Undecylenic acid, calcium undecylenate, zinc undecylenate may be used individually or in any ratio which provides a total undecylenate concentration of 10 to 25% Haloprogin 1% Any single antifungal active mentioned above with hydrocortisone or hydrocortisone acetate .5 to 1% Any single antifungal active mentioned above with any single keratolytic active agent recognized as safe and effective by the OTC final monograph |

| PRODUCT | FORMULA 5 | % W/W | ACTIVE MATERIALS |
|---|---|---|---|
| Diaper Rash Lotion | Alcohol SDA 40 200° Ethocel Standard 100 Premium Panthenol Alkyldimethyl benzyl-ammonium chloride Hydrocortisone acetate | 97.75 1.00 .05 .25 .05 | Alkyldimethyl benzylammonium chloride Allantoin (5-ureidohydantoin) Aluminum acetate Aluminum hydroxide Aluminum dihydroxy allantoinate Amylum Aromatic oils Balsam peru Balsam peru oil Beeswax Benzethonium chloride Benzocaine Bicarbonate of soda Bismuth subcarbonate Bismuth subnitrate Boric acid Calamine (prepared calamine) Calcium carbonate Calcium undecylenate Camphor Casein Cellulose Chloroxylenol (p-chloro-m-xylenol) Cod liver oil Corn starch Cysteine hydrochloride Dexpanthenol (D-panthenol) Dibucaine Diperodon hydrochloride Eucalyptol Glycerin Hexachlorophene Hydrocortisone acetate |

-continued

|  |  |  | 8-Hydroxyquinoline |
|---|---|---|---|
|  |  |  | Iron oxide |
|  |  |  | Lanolin |
|  |  |  | Live yeast cell derivative |
|  |  |  | Magnesium carbonate |
|  |  |  | Menthol |
|  |  |  | Methapyrilene |
|  |  |  | Methionine |
|  |  |  | DL-Methionine |
|  |  |  | Methylbenzethonium chloride |
|  |  |  | Microporous cellulose |
|  |  |  | Mineral oil |
|  |  |  | Oil of cade |
|  |  |  | Oil of Eucalyptus |
|  |  |  | Oil of lavender |
|  |  |  | Oil of peppermint |
|  |  |  | Oil of white thyme |
|  |  |  | Panthenol |
|  |  |  | Para-chloromercuriphenol |
|  |  |  | Petrolatum |
|  |  |  | Phenol |
|  |  |  | Phenylmercuric nitrate |
|  |  |  | Pramoxine hydrochloride |
|  |  |  | Protein hydrolysate (composed |
|  |  |  | of L-leucine, L-isoleucine, |
|  |  |  | L-methionine, L-phenylalanine, |
|  |  |  | and L-tyrosine) |
|  |  |  | Resorcinol (resorcin) |
|  |  |  | Salicylic acid |
|  |  |  | Shark liver oil |
|  |  |  | Silicone |
|  |  |  | Sorbitan monostearate |
|  |  |  | Starch |
|  |  |  | Talc |
|  |  |  | Tetracaine |
|  |  |  | Vitamin A |
|  |  |  | Vitamin A palmitate |
|  |  |  | Vitamin D |
|  |  |  | Vitamin $D_2$ |
|  |  |  | Vitamin E (DL-alpha-tocopheryl acetate) |
|  |  |  | White petrolatum |
| PRODUCT | FORMULA 6 | % W/W | ACTIVE MATERIALS |
| Poison Ivy, | Alcohol SDA 40 200° | 68.00 | Alcohol |
| Oak and Sumac | Ethocel Standard | 1.0 | Allantoin (5-ureidohydantoin) |
| Preparations | 100 Premium |  | Beechwood creosote |
|  | Lidocaine | 1.0 | Benzethonium chloride |
|  | Calamine | 10.0 | Benzocaine |
|  | Volatile Silicone | 20.00 | Benzyl alcohol |
|  |  |  | Bicarbonate of soda |
|  |  |  | Bichloride of mercury |
|  |  |  | Bithionol |
|  |  |  | Calamine |
|  |  |  | Camphor |
|  |  |  | Cetyldimethylbenzylammonium chloride |
|  |  |  | Chloral hydrate |
|  |  |  | Chloroform |
|  |  |  | Chloropheniramine maleate |
|  |  |  | Dimethyl polysiloxane |
|  |  |  | Diperodon hydrochloride |
|  |  |  | Diphenhydramine hydrochloride |
|  |  |  | Endothermic hectorite |
|  |  |  | Ferric chloride |
|  |  |  | Glycerin |
|  |  |  | Hexachlorophene |
|  |  |  | Hydrogen peroxide |
|  |  |  | Hydrous zirconia |
|  |  |  | Iron oxide |
|  |  |  | Isopropyl alcohol |
|  |  |  | Lanolin |
|  |  |  | Lead acetate |
|  |  |  | Lidocaine |
|  |  |  | Menthol |
|  |  |  | Merbromin |
|  |  |  | Oil of eucalyptus |
|  |  |  | Oil of turpentine |
|  |  |  | Panthenol |
|  |  |  | Parethoxycaine |
|  |  |  | Phenol |
|  |  |  | Phenyltoloxamine dihydrogen |

| PRODUCT | FORMULA 7 | % W/W | ACTIVE MATERIALS |
|---|---|---|---|
| | | | citrate |
| | | | Polyvinyl pyrrolidone |
| | | | Pyrilamine maleate |
| | | | Salicylic acid |
| | | | Tannic acid |
| | | | Tincture of impatients bi-flora |
| | | | Triethanolamine |
| | | | Zinc acetate |
| | | | Zirconium oxide |
| | | | Zyloxin |
| Fever Blister Lotion | Alcohol SDA 40 | 85.00 | Alcohol |
| | Ethocel Standard 100 Premium | 1.00 | Allantoin (5-ureidohydantoin) |
| | | | Ammonia |
| | Camphor | 10.00 | Ammonium carbonate |
| | Phenol | 4.00 | Benzalkonium chloride |
| | | | Benzocaine |
| | | | Camphor |
| | | | Lanolin |
| | | | Lanolin alcohol |
| | | | Menthol |
| | | | Mineral oil |
| | | | Paraffin |
| | | | Peppermint oil |
| | | | Petrolatum |
| | | | Phenol |
| | | | Sorbitan sesquioleate |
| | | | Soya sterol |
| | | | Tannic acid |

| PRODUCT | FORMULA 8 | % W/W | ACTIVE MATERIALS |
|---|---|---|---|
| Insect Bite Lotion | Alcohol SDA 40 200° | 95.75 | Alcohol |
| | Ethocel Standard 100 Premium | 1.00 | Ammonium hydroxide |
| | | | Aqua ammonia |
| | Calamine | 3.00 | Bicarbonate of soda |
| | Camphor | .25 | Calamine |
| | | | Camphor |
| | | | Ethoxylated alkyl alcohol |
| | | | Ferric chloride |
| | | | Fluid extract ergot |
| | | | Menthol |
| | | | Obtundia surgical dressing |
| | | | Oil of turpentine |
| | | | Peppermint oil |
| | | | Phenol |
| | | | Pyrilamine maleate |
| | | | Sodium borate |
| | | | Triethanolamine |
| | | | Zinc oxide |
| | | | Zirconium oxide |

| PRODUCT | FORMULA 9 | % W/W | ACTIVE MATERIALS |
|---|---|---|---|
| Sunscreen/ Insect Repellent Lotion | Alcohol SDA 40 200° | 33.5 | Diethyl toluamide |
| | Ethocel Standard 100 Premium | 1.0 | Aminobenzoic acid 5–15% |
| | | | Cinoxate 1 to 3% |
| | Volatile Silicone | 32.0 | Diethanolamine p-methoxy- |
| | Escalol 507 | 8.0 | cinnamate 8 to 10% |
| | Parsol MCX | 5.0 | Digalloyl trioleate 2 to 5% |
| | Ethyl salicylate | 5.0 | Dioxybenzone 3% |
| | Diethyl toluamide | 15.0 | Ethyl 4 (bis(hydroxypropyl)) |
| | Fragrance | .5 | aminobenzoate 1 to 5% |
| | | | Ethylhexyl 2-cyano-3, 3-diphenylacrylate 7 to 10% |
| | | | Ethylhexyl p-methoxycinnamate 2 to 7.5% |
| | | | 2-Ethylhexyl salicylate |
| | | | Glyceryl aminobenzoate 2 to 3% |
| | | | Homosalate 4 to 15% |
| | | | Lawsone with dihydroxyacetone 3% DHA .25 Lawsone |
| | | | Menthyl anthranilate 3.5% to 5% |
| | | | Oxybenzone 2 to 6% |
| | | | Padimate A 1 to 5% |
| | | | Padimate O 1.4 to 8% |
| | | | 2-Phenylbenzimidiazole-5-sulfonic acid 1 to 4% |
| | | | Red petrolatum 30 to 100% |
| | | | Sulisobenzone 5 to 10% |
| | | | Titanium dioxide 2 to 25% |
| | | | Triethanolamine salicylate 5 to 12% |

-continued

| PRODUCT | FORMULA 10 | % W/W | ACTIVE MATERIALS |
|---|---|---|---|
| Analgesic, Anesthetic, Anti-pruritic Preparations | Alcohol SDA 40 200° Ethocel Standard 100 Premium Benzyl alcohol Hydrocortisone acetate | 88.75 1.00 10.00 .25 | Benzocaine 5 to 20% Butamben picrate 1% Dibucaine 0.25% to 1% Dibucaine hydrochloride 0.25 to 1% Dimethisoquin hydrochloride 0.3 to 0.5% Dyclonine hydrochloride 0.5 to 1% Lidocaine 0.5 to 4% Lidocaine hydrochloride 0.5 to 4% Pramoxine hydrochloride 0.5 to 1% Tetracaine 1 to 2% Tetracaine hydrochloride 1 to 2% Benzyl alcohol 10 to 33% Camphor 0.1 to 3% Camphor 3 to 10.8% and phenol 4.7% in a light mineral oil USP base Camphor 3 to 10.8 with meta-cresol 1 to 3.6% Juniper tar 1 to 5% Menthol 0.1 to 1% Phenol 0.5 to 1.5% Phenolate sodium 0.5 to 1.5% Resorcinol 0.5 to 3% Diphenhydramine hydrochloride 1 to 2% Tripelennamine hydrochloride 0.5 to 2% Hydrocortisone 0.25 to 0.5% Hydrocortisone acetate 0.25 to 0.5% Counterirritants: Produce redness Allyl isothicyanate 0.5 to 5% Strong ammonia solution 1 to 2.5% ammonia Methyl salicylate 10 to 60% Turpentine oil 6 to 50% Cooling: Camphor 3 to 11% Menthol 1.25 to 16% |

| PRODUCT | FORMULA 11 | % W/W | ACTIVE MATERIALS |
|---|---|---|---|
| Moisturizing Lotion Protective Hand Lotion | Alcohol SDA 40 200° Ethocel Standard 100 Premium Castor oil Volatile Silicone Fragrance | 45.5 1.00 3.00 50.00 00.5 | |

| PRODUCT | FORMULA 12 | % W/W | ACTIVE MATERIALS |
|---|---|---|---|
| Pre-electric and After Shave Lotion | Alcohol SDA 40 200° Ethocel Standard 100 Premium Isodecyl Neopentaoate Fragrance Volatile silicone | 72.00 1.00 4.0 3.0 20.00 | |

| PRODUCT | FORMULA 13 | % W/W | ACTIVE MATERIALS |
|---|---|---|---|
| Make-Up Lotion | Alcohol SDA 40 200° Ethocel Standard 100 Premium Veegum Iron, Iron oxides Titanium Dioxide Fragrance | 87.3 1.0 1.5 7.0 3.0 .2 | |

| PRODUCT | FORMULA 14 | % W/W | ACTIVE MATERIALS |
|---|---|---|---|
| Arthritis Lotion | Alcohol SDA 40 200° Ethocel 100 Standard Premium Methyl salicylate Isodecyl neo-pentanoate Volatile Silicone | 44.0 1.0 20.00 5.00 30.00 | Allyl isothiocyanate .5 to 5% Strong ammonia solution diluted to contain 1 to 2.5% ammonia Methyl salicylate 10 to 60% Turpentine oil 6 to 50% Camphor 3 to 11% |

|  |  |  | Menthol 1.25 to 16% |
|---|---|---|---|
|  |  |  | Histamine dihydrochloride 0.25 to .1% |
|  |  |  | Methyl nicotinate .25 to 1% |
|  |  |  | Capsaicin 0.025 to .25% |
|  |  |  | Capsicum oleoresin 0.025 to .25% |
|  |  |  | Capsicum containing 0.025 to .25% capsaicin |

| PRODUCT | FORMULA 15 | % W/W | ACTIVE MATERIALS |
|---|---|---|---|
| Hair Dye | Alcohol SDA 40 200° | 73.25 |  |
|  | Ethocel Standard 100 Premium | 1.00 |  |
|  | Klucel | .75 |  |
|  | Dyes | 2.00 |  |
|  | Glucan P-10 | 3.00 |  |
|  | Volatile Silicone | 20.00 |  |

| PRODUCT | FORMULA 16 | % W/W | ACTIVE MATERIALS |
|---|---|---|---|
| Deodorant Lotion | Alcohol SDA 40 200° | 69.75 | Triclosan |
|  | Ethocel 100 Standard Premium | 1.0 | Fragrance Benzethonium chloride |
|  | Triclosan | .25 |  |
|  | Volatile Silicone | 25.0 |  |
|  | Isodecyl neo-pentoanoate | 4.0 |  |

| PRODUCT | FORMULA 17 | % W/W | ACTIVE MATERIALS |
|---|---|---|---|
| Antiperspirant Lotion | Alcohol SDA 40 200° | 53.5 | Aluminum chlorohydrate polyethylene glycol complex |
|  | Ethocel 100 Standard Premium | 1.0 | Aluminum chlorohydrate propylene glycol complex |
|  | Volatile Silicone | 24.0 |  |
|  | Isodecyl neo-pentanoate | 1.5 |  |
|  | Aluminum chloro-hydrate propylene glycol complex | 20.0 |  |

| PRODUCT | FORMULA 18 | % W/W | ACTIVE MATERIALS |
|---|---|---|---|
| Astringent Lotion | Alcohol SDA 40 200° | 63.0 | Aluminum acetate, 2.5 to 5% |
|  | Ethocel Standard 100 Premium | 1.0 | Witch hazel, NF, XL |
|  | Aluminum Acetate | 3.0 |  |
|  | Volatile Silicone | 30.0 |  |
|  | Isodecyl Neopentanoate | 3.0 |  |

| PRODUCT | FORMULA 19 | % W/W | ACTIVE MATERIALS |
|---|---|---|---|
| Hemmorrhoid Lotion | Alcohol SDA 40 200° | 76.6 | Calamine 5 to 25% |
|  | Ethocel Standard 100 Premium | 1.0 | Menthol .25 to 1% |
|  | Alcloxa | 2.0 | Alcloxa .2 to 2% |
|  | Menthol | 0.4 | Witch hazel 10 to 50% |
|  | Volatile Silicone |  | Ephedrine Sulfate 2 to 25 milligrams in water per dosage unit |
|  |  |  | Epinephrine hydrochloride 100 to 200 milligrams in water per dosage unit |
|  |  |  | Phenylephrine hydrochloride 1.5 milligram in water per dosage unit |

| PRODUCT | FORMULA 20 | % W/W | ACTIVE MATERIALS |
|---|---|---|---|
| Antibiotic Lotion | Alcohol SDA 40 200° | 65.97 | Chlortetracycline hydro-chloride 30 milligrams per gram |
|  | Ethocel Standard 100 Premium | 1.0 | Neomycin sulfate 3.5 milligrams neomycin per gram |
|  | Volatile silicone | 30.0 | Oxytetracycline hydrochloride 30 milligrams per gram |
|  | Isodecyl neo-pentanoate | 3.0 | Tetracycline hydrochloride 30 milligrams per gram |
|  | Oxytetracycline hydro-chloride | .03 | Bacitracin 500 units per gram |
|  |  |  | Bacitracin zinc 500 units per gram |
|  |  |  | Polymyxin B sulfate 5000 to 10,000 units per gram (used in combination only) |

While the present invention has been set forth in terms of its specific embodiments, it will be understood that numerous variations will be obvious to those skilled in the art. Accordingly, the invention is to be broadly construed and limited only by the scope of the appended claims.

What is claimed is:

1. A composition which when applied to the skin provides a fine, thin substantive film characterized by cosmetically acceptable tactile properties, strong adherence to the skin and high resistance to removal by water or abrasion consisting essentially of (a) from about 0.1% to about 10.0% by weight of a cellulosic ether having an ethoxyl content above about 47% and (b) from about 20% to about 95% by weight of a lower aliphatic alcohol organic solvent for said cellulosic ether.

2. A composition as claimed in claim 1 wherein said cellulosic ether is a cellulose ethyl ether having an ethoxyl content of from about 48% to about 49.5%.

* * * * *